United States Patent [19]

Kim et al.

[11] Patent Number: 5,461,164
[45] Date of Patent: Oct. 24, 1995

[54] OXIDATIVE DESULFURIZATION AND HALOGENATION OF THIOACYLATED PYRAZOLOTRIAZOLE COMPOUNDS

[75] Inventors: Chang K. Kim, Pittsford; Francesco DeBellis, Rochester, both of N.Y.

[73] Assignee: Eastman Kodak Company, Rochester, N.Y.

[21] Appl. No.: 213,786

[22] Filed: Mar. 14, 1994

[51] Int. Cl.$^6$ .................................................. C07D 487/04
[52] U.S. Cl. ........................................................ 548/262.4
[58] Field of Search .......................... 548/262.4; 514/383

[56] References Cited

U.S. PATENT DOCUMENTS

| | | | |
|---|---|---|---|
| 3,725,067 | 4/1973 | Bailey et al. | 96/56.5 |
| 4,992,361 | 2/1991 | Bowne et al. | 430/558 |
| 5,055,586 | 10/1991 | Kim et al. | 548/262.4 |

FOREIGN PATENT DOCUMENTS

| | | |
|---|---|---|
| 0284239 | 9/1988 | European Pat. Off. . |
| 0284240 | 9/1988 | European Pat. Off. . |
| 0285274 | 10/1988 | European Pat. Off. . |
| 3101386 | 5/1988 | Japan . |
| 3101387 | 5/1988 | Japan . |
| 2101077 | 4/1990 | Japan . |
| 2201442 | 8/1990 | Japan . |
| 3258780 | 11/1991 | Japan . |
| 4021683 | 1/1992 | Japan . |
| 4041488 | 2/1992 | Japan . |

OTHER PUBLICATIONS

Research Disclosure–Aug. 1974–No. 12443 (3 pages).

Primary Examiner—Johann Richter
Assistant Examiner—Laura L. Stockton
Attorney, Agent, or Firm—Arthur E. Kluegel

[57] ABSTRACT

A process for the desulfurization, and halogenation of a 1-acyl-7-acylthio-3,6-disubstituted-1H-pyrazolo[ 5,1-c]-1, 2,4-triazole first compound comprises reacting the compound with an excess of a halogenating agent whereby a 3,6-disubstituted-7,7-dihalo-1H-pyrazolo[ 5,1-c]-1,2,4-triazole compound is formed.

18 Claims, No Drawings

OXIDATIVE DESULFURIZATION AND HALOGENATION OF THIOACYLATED PYRAZOLOTRIAZOLE COMPOUNDS

FIELD OF THE INVENTION

This invention relates to an improved process for the desulfurization and halogenation of thioacylated pyrazolotriazole compounds.

BACKGROUND OF THE INVENTION

Pyrazolotriazoles, such as those described herein are useful magenta couplers for photographic products; however, they are difficult to synthesize. Only a few synthetic routes are known. One of the preferred synthetic routes involves preparation of the triazolothiadiazines (III) and subsequent desulfurization reaction to give the pyrazolotriazoles (IV). U.S. Pat. No. 5,055,586 of Kim et al. fully describes the state of the art and its contents are incorporated herein by reference. The triazolothiadiazines (III) can be prepared in two ways: the first, by reaction of 4-amino-5-mercapto-3-substituted- 1,2,4-triazoles with alpha-haloketones, or the second, by reaction of 2-hydrazino-5-substituted-1,3,4-thiadiazines with acyl halides and subsequent dehydrative ring closure. Both the triazoles and the thiadiazines are readily available from thiocarbohydrazide.

The following schematic shows the known process for the further treatment of the thiadiazine. In the known process, the first step is a ring contraction reaction of (III) by heating in acetic anhydride to give 1-acetyl-7-acetylthio-3,6-disubstituted- 1H-pyrazolo[5,1-c]-1,2,4-triazoles (I); the second step is hydrolysis of acetyl groups and desulfurization at the same time with hydrochloric acid to give the desired compound (IV); the third step, to obtain a halogenated material, is to halogenate (IV) to obtain (II).

pyrazolo[5,1-c]-1,2,4-triazoles (II).

The hydrolysis and desulfurization reaction with hydrochloric acid, however, generates many sulfur-containing impurities as by-products as more fully disclosed in U.S. Pat. No. 5,055,586. Moreover, in the mentioned patent, it is proposed to overcome the problems related to by-product generation by the inclusion of hypophosphorus acid in the hydrolysis step. However, it has been found that the use of hypophosphorus acid results in formation of hydrogen sulfide as a by-product. In view of the gaseous and toxic nature of the hydrogen sulfide and its ill odor, its generation presents an undesirable environmental, safety and health risk requiring extensive precautions and controls.

It is therefore a problem to be solved to provide a process for the desulfurization and halogenation of thioacylated pyrazolotriazole compounds that produces the desired product in good yield and where the sulfur by-products are reduced in quantity, are in readily removable oxidized form, and are substantially free of hydrogen sulfide.

SUMMARY OF THE INVENTION

The present invention provides a process for the desulfurization, and halogenation of a 1-acyl-7-acylthio- 3,6-disubstituted-1H-pyrazolo[5,1-c]-1,2,4-triazole first compound which comprises reacting the compound with an excess of a halogenating agent whereby a 3,6-disubstituted-7,7-dihalo-1H-pyrazolo[5,1-c]-1,2,4-triazole compound is formed. In an overall conversion process, a thiadiazine is first subjected to acylation and ring contraction, desulfurized and halogenated in accordance with the invention, and then partially dehalogenated.

The invention provides an efficient process that produces the desired product in good yield and where the sulfur by-products are reduced in quantity, are in readily removable

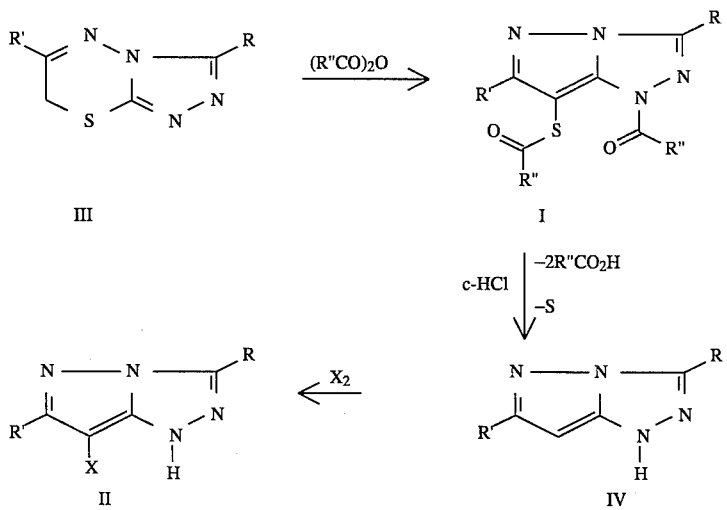

Thus the known process provides for heating in an anhydride to give 1-acyl-7-acylthio-3,6-disubstituted-1H-pyrazolo[5,1-c]-1,2,4-triazoles (I). Hydrolysis of acyl groups and desulfurization at the same time with concentrated hydrochloric acid gives 3,6-disubstituted-1H-pyrazolo-[5,1-c]-1,2,4-triazoles (IV). Subsequent halogenation of the Compound IV gives the 3,6-disubstituted-7-halo-1H- oxidized form, and are free of hydrogen sulfide.

DETAILED DESCRIPTION OF THE INVENTION

The invention provides a process for converting a 1-acyl-7-acylthio-3,6-disubstituted-1H-pyrazolo[5,1-c]-1,2,4-triazole of formula I:

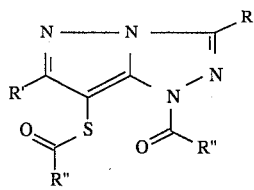

to a 3,6-disubstituted-7,7-dihalo-1H-pyrazolo[5,1-c]-1,2,4-triazole having formula V:

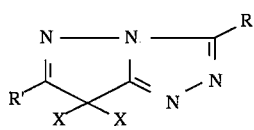

that can, in turn, be converted to a 3,6-disubstituted-7-halo-1H-pyrazolo[5,1-c]-1,2,4-triazole having formula II:

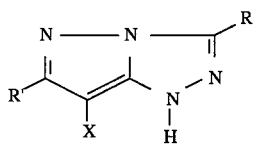

A schematic for the overall process extending from the thiadiazine to the monohalogenated triazole end product is represented as follows:

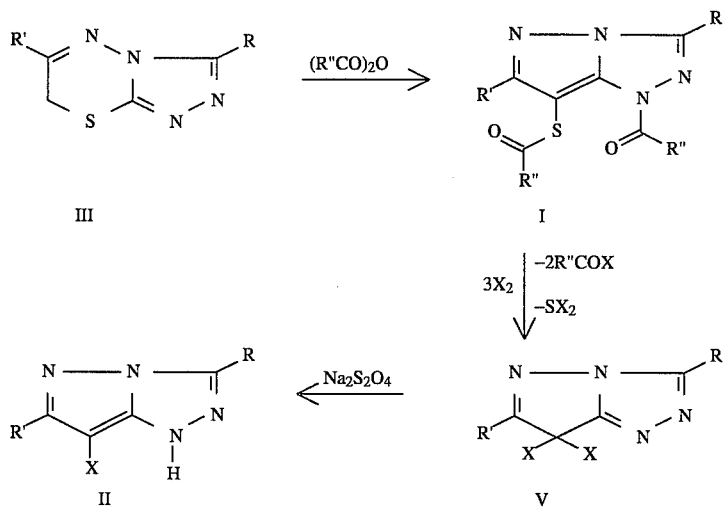

Besides forming the oxidized sulfur by-products and thus making the process environmentally safer, the use of the halogenating agent in the process of this invention offers several other advantages. For example, use of the halogenating agent produces the pyrazolotriazoles halogenated at the desired position, although it is usually doubly halogenated initially (See compound V). Since the 1-acyl-7-acylthio-3,6-disubstituted-1H-pyrazolo[5,1-c]-1,2,4-triazoles (I) formed by the ring contraction reaction from the corresponding triazolothiadiazines (III) may be used without isolation in the next desulfurization and halogenation reactions with the halogenating agents, the conversion from Compound III to Compound V is a one-pot process and therefore greatly simplified. The doubly halogenated Compound V is readily converted to the desired mono-halogenated pyrazolotriazoles (II) by simple treatment with a mild reducing agent such as ascorbic acid or sodium dithionite.

In the compounds used as starting materials in this invention, and the compounds produced as intermediates as well as products, all represented by formulas I, II, III, and V above, R and R' are "inert substituents". For the purpose of this invention, an "inert substituent" or "inert group" is defined by having the following characteristics:

(1) It is stable, or substantially stable, under the process conditions employed; i.e., it does not decompose to an unwanted extent during process(es) employed in this invention.

(2) It is non-reactive, or substantially non-reactive toward the other reagents employed; i.e., it does not undergo an extraneous side reaction to an unacceptable extent with the other ingredient(s) used.

(3) It does not prevent, by steric hindrance or other mechanism or effect, the formation of a compound of this invention.

Thus, a wide variety of substituents may appear as R and/or R' in the above formulas. In other words, this invention is not critically dependent on the type(s) of groups designated as R and R', as long as the groups meet criteria (1), (2), and (3) above. Typically, R and R' are hydrocarbons, i.e., groups which are generally composed of carbon and hydrogen, with or without other substituent group(s). Alkyl, cycloalkyl, alkenyl, cycloalkenyl, aryl, aralkyl, heteroaryl, heterocyclic groups containing oxygen, sulfur, or nitrogen as the heteroatom which meet the above criteria can be present in the compound of this invention. The alkyl or aryl group may contain other substituent(s) such as halogen, other alkyl or aryl, nitro, amino or substituted amino, sulfide, sulfoxide, sulfone, hydroxy, alkoxy, aryloxy, or like. For convenience, R and R' are usually groups having up to about 40 carbon atoms.

Suitably, R and R' are alkyl groups, including straight or branched chain or cyclic alkyl, either unsubstituted or substituted with one or more substituents, such as: nitro; halogen; hydroxyl; cyano; carboxyl and its salts; and groups which may be further substituted, such as alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, α- or β-naphthyloxy, and 4-tolyloxy; carbonamido, such as acetamido, benzamido, butyramido, tetradecanamido, a-(2,4-di-t-pentyl-phenoxy)acetamido, a-(2,4-di-t-pentylphenoxy)butyramido, a-(3-pentadecylphenoxy)hexanamido, a-(4-hydroxy-3-t-butylphenoxy)tetradecanamido, 2-oxo-pyrrolidin-1-yl, 2-oxo-5-tetradecyl-pyrrolin- 1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylcarbonylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl)carbonylamino, p-dodecylphenylcarbonylamino, p-toluylcarbonylamino, N-methylureido, N,N-dimethylureido, N-methyl-N-dodecylureido, N-hexadecylureido, N, N-dioctadecylureido, N,N-dioctyl-N'-ethylureido, N-phenylureido, N,N-diphenylureido, N-phenyl-N-p-toluylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-toluylsulfonamido, p-dodecylbenzenesulfonamido, N-methyltetradecylsulfonamido, and hexadecylsulfonamido; sulfamoyl, such as N-methylsulfamoyl, N,N-dipropylsulfamoylamino, N-ethylsulfamoyl, N,N-dipropylsulfamoyl, N-hexadecylsulfamoyl, N,N-dimethylsulfamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-toluylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-toluylsulfinyl; thio, such as ethylthio, octylthio, benzylthio, tetradecylthio, 2-(2,4-di-t-pentylphenoxy) ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1-(N-phenylimido)ethyl, N-succinimido or 3-benzylhydantoinyl; phosphate, such as dimethylphosphate and ethylbutylphosphate; phosphite, such as diethyl and dihexylphosphite; azo, such as phenylazo and naphthylazo; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

When the radical R" appears in compounds of this invention, it represents lower alkyl radicals, preferably those having up to about 7 carbon atoms. Methyl is particularly suitable for this substituent. The radical X in the compounds of this invention represents either chlorine or bromine.

The R, R', R", and X radicals are generally selected according to the properties that they confer on the compounds, and/or the role that they play in the selected utility. For example, since the radical R" appears in a group which is to be subsequently removed, R" is preferably selected from a methyl, ethyl, or other lower alkyl group in order to lower process costs. On the other hand, the size or nature of the group may be selected to confer some physical or chemical property, such as a desired degree of solubility or compatibility with other ingredients in a mixture in which the product is used.

As indicated above, Compound I can be prepared by a ring contraction reaction by heating in an anhydride. A detailed description of this ring contraction reaction using the anhydride as acylating agent is shown in the U.S. Pat. No. 5,055,586.

Most suitably, the process is conducted under strictly anhydrous conditions to prevent unwanted hydrolysis. This can be achieved by using excess anhydride in solvent quantities. After the ring contraction reaction is complete, the desulfurization and halogenation reaction with halogenating agents can be conducted on the reaction mixture produced. Although the Compound I can be isolated using techniques within the skill of the art, the isolation of the Compound I is not preferred since it is pure enough to use in the next step and already in anhydrous medium that prevents hydrolysis and thus minimizes the formation of unwanted sulfur-containing organic impurities.

The halogenating agent for the process of this invention is selected on its availability and cost. Chlorine, bromine, sulfuryl chloride, sulfuryl bromide, N-chlorosuccinimide (NCS), N-bromosuccinimide (NBS), 1,3-dichloro-5,5-dimethylhydantoin (DCDMH), or 1,3-dibromo-5,5-dimethylhydantoin (DBDMH) can be used. Most preferred are sulfuryl chloride for chlorinated pyrazolotriazoles and bromine for brominated pyrazolotriazoles.

The halogenating agent may suitably be used in an excess, at least 3 equivalents of the triazole compound to be halogenated, in order to get desirable yields. Preferably 3-5 equivalents of halogenating agent are used.

The desulfurization and halogenation is generally conducted at a temperature which gives a reasonable rate of reaction, but the reaction temperature is dependent on the halogenating agent used. For example, gaseous chlorine may be used at a lower temperature, generally lower than room temperature. Liquid halogenating agents such as bromine, sulfuryl chloride, and sulfuryl bromide may be used in a temperature lower than room temperature or at somewhat elevated temperatures, generally from room temperature to 100° C., if necessary. Solid halogenating agents such as NCS, NBS, DCDMH, and DBDMH may be used at any temperature including those as high as 200° C., so long as it does not cause any unwanted extraneous side reactions.

Ambient pressures are preferred, however, some elevated pressures can be used when gaseous chlorine is used as halogenating agent, or if the reaction is to be conducted at a temperature above the boiling point of halogenating agent or one or more of the constituents in the reaction mixture.

The reaction time is not a truly independent variable, but is at least somewhat dependent on the reaction temperature and the inherent reactivity of the reactants. In general, the reaction times of from 0.5 to 20 hours are sufficient.

After the desulfurization and halogenation reaction is complete, the doubly halogenated pyrazolotriazole can be isolated from the reaction mixture by a known technique such as crystallization or extraction. The oxidized sulfur by-products derived from acylthio group is usually a mixture of elemental sulfur, R'—CO—S—X, $SX_2$, $S_2X_2$, and the like, all of which are odorless and soluble in most of organic solvents and thus remained in solution when the product is crystallized. The exact nature and composition of sulfur by-products is not known.

The dihalogenated pyrazolotriazoles are readily converted to the desired mono-halogenated pyrazolotriazoles by a known technique such as treatment with a mild reducing agent, like ascorbic acid or sodium dithionite, as shown in the following examples. A "mild reducing agent" herein is one which has reducing strength sufficient to reduce one but not both of the halogens atoms of the dihalogenated compounds. The mild reducing agent may be suitably selected for availability and cost. Suitable examples of such reducing agents are ascorbic acid and its salts, hypophosphorous acid, phosphorous acid and its salts, bisulfite, sulfite or dithionite alkali metal salts, and hydroquinone. Most suitable are the alkali metal salts of ascorbic acid or dithionite.

The following examples will serve to illustrate the invention:

EXAMPLE 1:

Synthesis of 7-Chloro-6-methyl-3-[1-(4-nitrophenoxy) tridecyl]-1H-pyrazolo[5,1-c]-1,2,4-triazole A mixture of 47.4 g (0.10 mol) of 6-methyl-3-[1-(4-nitrophenoxy) tridecyl]-7H-1,2,4-triazolo[3,4-b][1,3,4]thiadiazine and 180 g of acetic anhydride is heated under reflux for 16 hours. The reaction mixture is cooled to room temperature and 54 g (0.40 mol) of sulfuryl chloride is added. After stirring at room temperature for 1 hour, the reaction mixture is poured in 300 ml of ice water with vigorous stirring and the product is extracted with ethyl acetate (300 ml). The ethyl acetate solution is washed with water and concentrated to an oil. The oil is dissolved in 150 ml of methanol and to this is added 17.6 g (0.10 mol) of ascorbic acid and 15.8 g (0.20 mol) of pyridine. The mixture is stirred at 50° C. for 5 hours and cooled to room temperature. To the mixture is added 200 ml of water with stirring and precipitated product is collected and washed with water and cold methanol. The dried crude product is slurried in 200 ml of warm heptane for an hour, cooled, collected, and recrystallized from methanol to give 38.6 g (81%) of 7-chloro-6-methyl-3-[1-(4-nitrophenoxy)tridecyl]-1H-pyrazolo[5,1-c]-1,2,4-triazole with 99.1 A % by HPLC.

EXAMPLE 2:

Synthesis of 7-Chloro-6-t-butyl-3-(3-nitro-2,4,6-trimethyl)phenyl- 1H-pyrazolo[5,1-c]-1,,2,4-triazole With 6-t-butyl-3-(3-nitro-2,4,6-trimethyl)phenyl- 7H-1,2,4-triazolo[3,4-b][1,3,4]-thiadiazine, the reaction is carried out following a procedure similar to that described in Example 1. There is obtained 7-chloro-6-t-butyl-3-(3-nitro-2,4,6-trimethyl)phenyl- 1H-pyrazolo[5,1-c]-1,2,4-triazole in 85% yield with 98.4 A % by HPLC.

EXAMPLE 3:

Synthesis of 7-Chloro-3-(1-chloroethyl)-6-methyl-1H-pyrazolo[5,1-c]-1,2,4-triazole With 3-(1-chloroethyl)-6-methyl-7H-1,2,4triazolo-[3,4-b][1,3,4]thiadiazine, the reaction is carried out following a procedure similar to that described in Example 1. There is obtained 7-chloro-3-(1-chloroethyl)-6-methyl-1H-pyrazolo [5,1-c]-1,2,4-triazole in 71% yield with 98 A % by HPLC.

The invention has been described above with particular reference to preferred embodiments thereof. A skilled worker being aware of the above detailed description can make many modifications or substitutions without departing from the scope or spirit of this invention.

What is claimed is:

1. A process for the desulfurization, and halogenation of a 1-acyl-7-acylthio-3,6-disubstituted- 1H-pyrazolo[5,1-c]-1,2,4-triazole first compound comprising reacting said compound with an excess of a halogenating agent whereby a 3,6-disubstituted- 7,7-dihalo-[7]1H-pyrazolo[5,1-c]-1,2,4-triazole compound is formed.

2. The process of claim 1 wherein the halogenating agent is initially present in an amount sufficient to provide at least three moles of halogen per mole of first triazole compound.

3. The process of claim 2 wherein the halogenating agent is initially present in an amount sufficient to provide from three to five moles of halogen per mole of first triazole compound.

4. The process of claim 1 wherein the halogenating agent is a chlorinating or brominating agent.

5. The process of claim 1 wherein said halogenating agent is selected from the group consisting of chlorine, sulfuryl chloride, bromine, sulfuryl bromide; N-chlorosuccinimide (NCS), N-bromosuccinimide (NBS), 1,3-dichloro-5,5-dimethylhydantoin (DCDMH), and 1,3-dibromo-5,5-dimethylhydantoin (DBDMH).

6. The process of claim 5 wherein said halogenating agent is sulfuryl chloride or bromine.

7. The process of claim 1 wherein the reaction with said halogenating agent is performed under anhydrous conditions.

8. A process for converting a 3,6-disubstituted- 7H-1,2,4-triazolo[3,4-b][1,3,4]thiadiazine to the corresponding 3,6-disubstituted- 7-halo-1H-pyrazolo[5,1-c]-1,2,4-triazole including the steps of first acylating and ring contracting said thiadiazine by heating and then reacting the resulting product with a halogenating agent as described in any one of claims 1 through 7 to form a halogenated product.

9. The process of claim 8 wherein the process includes the additional subsequent step of partially dehalogenating the product by reacting the dihalogenated product with a mild reducing agent.

10. The process of claim 9 wherein the mild reducing agent is selected from ascorbic acid and its alkali metal salts, hypophosphorous acid and its alkali metal salts, alkali metal salts of bisulfite, sulfite, and dithionite, and hydroquinone.

11. The process of claim 10 wherein the mild reducing agent is ascorbic acid or alkali metal salts of dithionite.

12. The process of claim 8 wherein the thiadiazine is 6-methyl-3-[1-(4-nitrophenoxy)tridecyl]-7H-1,2,4-triazolo [3,4-b][1,3,4]thiadiazine.

13. In a process for the preparation of a 3,6-disubstituted-7-halo-1H-pyrazolo-[5,1-c]-1,2,4-triazole from the corresponding 1-acyl-7-acylthio-3,6-disubstituted- 1H-pyrazolo[5,1-c]-1,2,4-triazole by oxidative desulfurization and halogenation;

the improvement which comprises conducting the desulfurization in the presence of an excess of halogenating agent.

14. In a process for the preparation of a 3,6-disubstituted-7-halo-1H-pyrazolo-[5,1-c]-1,2,4-triazole from the corresponding 3,6-disubstituted-7H-1,2,4-triazolo-[3,4-b][1,3,4]thiadiazine by ring contraction with heat and acylation to give a thioacylated pyrazolotriazole followed by oxidative desulfurization and halogenation of the acylated intermediate;

the improvement which comprises (1) conducting the desulfurization in the presence of an excess of halogenating agent, whereby a 3,6-disubstituted-7,7-dihalo-1H-pyrazolo[5,1-c]-1,2,4-triazole is obtained, and then (2) converting said dihalo compound to 3,6-disubstituted-7-halo-1H-pyrazolo[5,1-c]-1,2,4-triazole by partial dehalogenation.

15. The process of claim 14 wherein the desulfurization of the thioacylated pyrazolotriazole is conducted without its separation from the reaction medium.

16. The process of claim 14 wherein said partial dehalogenation step is performed in the presence of a mild reducing agent.

17. The process of claim 14 wherein the resulting triazole is 7-chloro-6-methyl-3-[1-(4-nitrophenoxy)tridecyl]-1H-pyrazolo[5,1-c]-1,2,4-triazole.

18. The process of claim 14 wherein the resulting triazole is 7-chloro-6-t-butyl-3-(3-nitro-2,4,6-trimethyl)phenyl-1H-pyrazolo[5,1-c]-1,2,4-triazole.

* * * * *